(12) United States Patent
Kiss et al.

(10) Patent No.: US 7,842,494 B2
(45) Date of Patent: Nov. 30, 2010

(54) MICRO-ORGANISMS FOR THE TREATMENT OF SOIL AND PROCESS FOR OBTAINING THEM

(75) Inventors: Gyorgy Botond Kiss, Szeged (HU); Istvan Ott, Budapest (HU)

(73) Assignee: Agro.Bio Hungary KFT., Budapest (HU)

( * ) Notice: Subject to any disclaimer, the term of this patent is extended or adjusted under 35 U.S.C. 154(b) by 1792 days.

(21) Appl. No.: 10/486,747

(22) PCT Filed: Aug. 12, 2002

(86) PCT No.: PCT/HU02/00081

§ 371 (c)(1),
(2), (4) Date: Oct. 14, 2004

(87) PCT Pub. No.: WO03/016241

PCT Pub. Date: Feb. 27, 2003

(65) Prior Publication Data

US 2005/0060930 A1 Mar. 24, 2005

(30) Foreign Application Priority Data

Aug. 13, 2001 (HU) .................................... 0103294

(51) Int. Cl.
*A01N 63/00* (2006.01)
*C12N 1/20* (2006.01)
(52) U.S. Cl. .................. 435/252.5; 424/93.46
(58) Field of Classification Search .............. None
See application file for complete search history.

(56) References Cited

FOREIGN PATENT DOCUMENTS

| WO | WO 84/01686 A1 | 5/1984 |
|---|---|---|
| WO | WO 96/34840 A1 | 11/1996 |
| WO | WO 98/37038 A2 | 8/1998 |
| WO | WO 99/09834 A2 | 3/1999 |
| WO | WO 00/34440 A1 | 6/2000 |

OTHER PUBLICATIONS

Grichko et al., Plant Physiol. Biochem. 39 (2001) 11-17.*
Mishra et al., Journal of Biotechnology 75 (1999) 71-75.*
Seong et al., 1991. Growth, survival, and root colonisation of plant growth beneficial *Pseudomonas fluorescens* ANP15 and *Pseudomonas aeruginosa* 7NSK2 at different temperatures,.Soil Biol. Biochem. 23:423-428.*
Rose AH, Evison LM. Studies on the Biochemical Basis of the Minimum Temperatures for Growth of Certain Psychrophilic and Mesophilic Micro-Organisms. J Gen Microbiol. Jan. 1965;38:131-141.*
Slininger et al ., Appl Microbiol Biotechnol (1996) 45:391-398.*

* cited by examiner

*Primary Examiner*—Irene Marx
(74) *Attorney, Agent, or Firm*—Saliwanchik, Lloyd & Saliwanchik

(57) ABSTRACT

The present invention relates to product(s) containing living microorganism(s) suitable for soil treatment, microorganisms multiplying under different climatic and natural circumstances, as well as procedures for the production of the products, and procedures for the treatment of the soil and plants with the products. More particularly, the invention relates to a procedure for preparing the products from any of the microorganisms specified below, or from the mixture thereof. Furthermore, the invention relates to a procedure for the creation of the cultures of the microorganisms to be used. The subject invention also pertains to the microorganisms themselves. More particularly, the invention relates to a procedure for the treatment of the soil and the plants with a product containing at least one of the microorganisms selected from *Azospirillum brasilense* ssp. SW51 (NCAIM /P/ B 001293), *Azotobacter vinelandii* ssp. M657 (NCAIM /P/B 001292), *Pseudomonas fluorescens* var. SW11 (NCAIM /P/ B 001296), *Bacillus polymyxa* var. SW17 (NCAIM /P/ B 001295), *Bacillus megaterium* var. M326 (NCAIM /P/ B 001291), *Micrococcus roseus* ssp. A21 (NCAIM /P/B 001294), *Bradyrhizobium japonicum* var. PH25 (NCAIM /P/ B 001302), and *Streptomyces albus* var. 0003 LP (NCAIM /P/ B 001301), and furthermore the products multiplying and existing in the environment of the plant in question, containing the listed microorganisms and their production.

16 Claims, No Drawings

MICRO-ORGANISMS FOR THE TREATMENT OF SOIL AND PROCESS FOR OBTAINING THEM

This application is the U.S. national stage application of International patent application No. PCT/HU02/00081, filed Aug. 12, 2002.

TECHNICAL FIELD

The present invention relates to product(s) containing alive micro-organism(s) suitable for soil treatment, micro-organisms multiplying under different climatic and natural circumstances, as well as the procedure for the production of the products, furthermore procedure for the treatment of the soil and plants with the products.

More detailed, the invention relates to a procedure for preparing the products from any of the micro-organisms specified below, or from the mixture thereof.

Furthermore, the invention relates to a procedure for the creation of the cultures of the micro-organisms to be used. Subject of the invention are the micro-organisms themselves, as well.

More detailed, the invention relates to a procedure for the treatment of the soil and the plants with a product containing at least one of the micro-organisms *Azospirillum brasilense* ssp. SW51 (NCAIM /P/ B 001293), *Azotobacter vinelandii* spp. M657 (NCAIM /P/ B 001291), *Pseudomonas fluorescens* var. SW11 (NCAIM /P/ B 001296), *Bacillus polymyxa* var. SW17 (NCAIM /P/ B 001295/, *Bacillus megaterium* var. M326 (NCAIM /P/ B 001301/-, furthermore the products multiplying and existing in the environment of the plant in question, containing the listed micro-organisms and their production.

BACKGROUND ART

The natural medium of the soil is the self-regulating ecosystem of the plants and micro-organisms, under natural circumstances, the existence of the former determines that of the other ones. When the balance developed in the course of the evolution is altered by human activities (deep ploughing, natural and artificial fertilisation, use of plant-protecting agents, etc.) in its structure and function, changes of non foreseeable effect can occur. For the development of the micro-organism populations needed for the optimal cultivation of a given cultivated plant, on the different soils and under different climatic circumstances, a selection time lasting for long years is needed. The determinant micro-organisms of the favourable micro-organism population, however, can be transported in the soil and the circumstances needed for the optimal cultivation can be created within one-two days. The result of this is the higher yield, without the harmful upsetting of the natural ecosystem. The useful and dominant micro-organisms existing in the environment of a given plant important from economic point of view can be determined by laboratory experiments and these can be individually multiplied, produced by industrial methods, and can be brought back in the soil in proper proportion.

Important regularities can be discovered in the ecosystem of the soil and micro-organisms. The number of the micro-organisms is different and different species can be identified in the immediate environment of the root system of the living plants (rhysosphere) and the germinating seeds (spermatosphere) than more remote from these. The propagation of the bacteria in the environment of the root is influenced by many factors. These factors depend on the region, quality of the soil, composition of the micro-organism population, and on the climatic circumstances.

The carbon source to be found in the soil comes into being primarily and in the overwhelming majority by using the solar energy, with photosynthesis.

The nitrogen cycle is more complicated than that of the carbon. On the transformation of nitrogen, biological and chemical processes have an effect. In the nature, the gaseous nitrogen in a so-called inert condition is dominant, and the so-called fixed nitrogen (nitrate, nitrite, ammonia) is present in a limited quantity.

For the mineralization of the nitrogen gas first of all the biological nitrogen binding is responsible. Since over one hectare the quantity of the molecular nitrogen amounts to $6$-$7 \times 10^8$ tons, this means an inexhaustible source for the nitrogen bound. The interest of the experts is directed towards the nitrogen binding living beings, i.e. towards the living beings, which can reduce the molecular nitrogen to ammonia since, among others, the knowledge of these micro-organisms and the adequate utilisation of their properties can ensure, in an environment friendly manner, the world-wide ceasing of the hunger.

Some nitrogen binding bacteria fix the nitrogen in free living condition but numerous bacteria are capable of nitrogen fixing only combined with other, higher plants.

The phosphorousous cycle, contrary to that of the nitrogen, is practically closed under natural circumstances. The input and output are identical, the flow is slight, the air won't be contaminated with phosphorousous. Finally, this element accumulates in the waters, seas, and only a slight quantity of this gets back to the land (for instance in the form of guano).

In the living cells of the soil the phosphorousous accumulates in organic compounds, the mineralization of these takes place with a high speed (3-8 $g/m^2$/year). The solubility—so their accessibility for the plants—of the arising phosphorousous compounds is different, merely 5% of the 400-1200 mg phosphorousous detectable in each 1 kg of the average soils is available. The turnover of certain phosphorousous compounds is 500-2000 years.

By transporting some phosphonolytic micro-organism groups in the soil, the complex phosphorousous compounds, which are not accessible for the plant, can be brought in solution. If the micro-organisms brought in the soil "function", and the mineral contents of the soil are satisfactory, the use of the fertilizers containing phosphate is not necessary or can be considerably reduced.

For growth, the plants need—especially at the time of the ripening of the crop—potassium of a considerable quantity. The plant cultivators bring the potassium in the soil by feeding of fertilizer with potassium content. This fertiliser can be made available from the potassium minerals by means of the micro-organisms releasing the potassium ion.

As far as the plants are concerned, the micro-organisms multiplying in the soil biosynthetize physiologically active compounds, out of these the most important compounds being: phytohormones, auxins (indole-3-acetic acid), ethylene, gibberellines, kinetins, etc. Some *Pseudomonas* groups, in the presence of iron of a slight quantity, produce so-called siderophores, which can collect the iron. As a consequence of this, the other, phytopathogenic bacteria and fungi, since these cannot utilize the iron from the siderophores, suffer inhibition owing to the lack of iron, on the other hand, these siderophores, in soil with lack of iron, significantly stimulate the growth of the plants, since binding the iron, these directly provide the iron for the plant.

For the solution of the above, several technical versions had been elaborated; several micro-organisms are described in the special literature in full details.

Hungarian inventors disclosed the preparation of powdered nitrification cultures (Hungarian patent HU 143.391), *Azobacter chroococcum* and *Rhizobium meliloti* cultures (Hungarian patent HU 188.434), alga cultures (Hungarian patent HU 195.068) and *Azotobacter chroococcum* cultures again, as well as the preparation of the cultures of *Bacillus megaterium* micro-organisms (Hungarian patent HU 207.751). The *Azobacter chroococcum* had been deposited under the deposit No. 00238, the *Bacillus megaterium* under the serial No. NCAIM /P/ B 1140. More detailed, in Hungarian patents HU 188.434 and HU 207.751, the authors describe the fermentation turning out of the mixture of the above deposited micro-organisms. According to Hungarian patent HU 213 163 the authors complete the culture of the microorganisms of HU 207.751 with carboxy-methyl-cellulose. Hungarian inventors in HU 1671/96 describe cultures containing *Azospirillum lipoferum* ssp., *Azobacter vinelandi* sp., *Pseudomonas fluorescens* ssp. and *Bacillus megaterium* ssp. micro-organisms.

The application and effect of the micro-organisms applied in the mentioned procedures are limited by the fact that these, under different cultivation circumstances, in soils of various compositions, under different climatic circumstances, survive only for a short time, the environment and rhysosphere of the various plants not always create optimal conditions.

DISCLOSURE OF THE INVENTION

The basic purpose of the invention is the preparation of such soil micro-organism cultures, which, from plant cultivation and economic point of view, are of a favorable effect, and which, at the same time, can survive, multiply and exert their favorable effect in various soils and on various plants, under different climatic and cultivation circumstances.

It has surprisingly been found that the multiplying and survival the micro-organisms favorably influencing the development of the plant, fixing the nitrogen, mobilizing the phosphate, stimulating the growth of the plant, improving the soil structure, cultivated in the laboratories vary depending on the character of the soil, the temperature conditions and the plant in the immediate environment of the plant. Different micro-organism groups exert their effect in ciernozjom soil, in soil of low humus content, in loess, country or for instance in clayey soil environment. In the course of our experiments it has been proved that, however surprising it is, other micro-organism groups can multiply in the rhysosphere of the various plants, or near to it and to exert their effect there for a long time.

Therefore, experiments were performed for the isolation of such micro-organisms, which have a favorable effect in the environment of a given plant being important from economic point of view, as far as its cultivation is concerned. Additionally, experiments were also carried out for the isolation of the micro-organisms, which can mobilize the potassium ions and for the preparation of such micro-organisms—isolated from the soil and changed in laboratory, by mutation procedures—, which can propagate at the time of bringing in the soil, at a low temperature, as well, and which—however surprising even for the expert, too—can exert their effect.

Moreover, we have stated in the course of the experiments that certain micro-organisms producing polysaccharides, in a surprising manner, change the soil structure favorably from agricultural point of view, hereby improving the drought-resistance.

Summing up our experiment work, it was our aim to isolate such micro-organisms, which transmit nitrogen, phosphorous, potassium to the plants, biosynthetize vegetal growth hormones, biosynthetize polysaccharides improving soil structure, and which are able to propagate in the sowing period and in the countries of the colder climate, as well, and to exert their effect in various soils and plants. Furthermore we aimed to produce such preparations, the micro-organism contents of which, in the environment of the plant, in the rhysosphere, or directly among the vegetal cells, by fixing and mobilisation of elements of vital importance, as well as by the production of vegetal growth factors and polysaccharides in the given vegetal environment promote the development of a given plant or family of plants, as a consequence of which we can save, in an environment protecting manner, the use of fertiliser.

Subject of the present invention is the growing procedure referring to the listed micro-organisms, the preparations containing these, furthermore, the application of the preparation(s) containing the micro-organism(s) and concretely the micro-organisms.

The present invention is based on the recognition that for making the target preparations, the *Azospirillum brasilense* ssp. SW51 (NCAIM /P/ B 001293), *Azotobacter vinelandi* ssp. M657 (NCAIM /P/ B 001292), *Pseudomonas fluorescens* var. SW11 (NCAIM /P/ B 001296), *Bacillus polymyxa* var. SW17 (NCAIM /P/ B 001295/, *Bacillus megaterium* var. M326 (NCAIM /P/ B 001291), *Micrococcus roseus* ssp. A21 (NCAIM /P/ B 001294/, *Bradyrhizobium japonicum* var. PH25 (NCAIM /P/ B 001302/and *Streptomyces albus* var. 0003 LP (NCAIM /P/ B 001301/micro-organisms are the most convenient, which can multiply at the low temperature of the sowing period, which supply the nitrogen for the plants, mobilize phosphorous, potassium, biosynthesized growth hormones and polysaccharides, therefore we isolated these and elaborated a growing procedure for these.

In sense of the above, between 1998 and 1999, we isolated in Europe, from soils and the root environment of certain plants micro-organisms, tested in vitro their ability of nitrogen fixing, phosphate and potassium solubilizing, polysaccharide producing and biosynthesizing of vegetal hormones, systematically identified the selected micro-organisms, prepared such variants by mutation treatment, which propagate intensively at temperatures below 20° C. as well, for the cultivation of these elaborated a growing technology, and from their cultures preparations were made, and proved their effect on the vegetal development and the yields by greenhouse and field experiments.

*Azospirillum, Azotobacter, Bradyrhizobium, Pseudomonas, Bacillus, Streptomyces* and *Micrococcus* species and subspecies were isolated.

The least known *Azospirillum* species are the bacteria of Gram-negative variable colouring, living in the soil, which, under micro-aerofil circumstances (in the presence of 1-2% oxygen), in close connection with the root system of the plants, can reduce the nitrogen of the air to ammonia, then transmit it to the plants. Some groups biosynthetize vegetal hormones, too.

The *Azospirillum* groups were isolated from the root environment of maize, wheat, barley, rye grown on various arable lands of Europe, in various soils and of the grass of hayfields. The bacterium suspension deriving from the soil sample was dispersed on the Nfb(II) and MM culture medium of the composition given later on, then cultivated under microaerophylic conditions. After 72 hours, the *Azospirillum* cultures were identified. The *Azospirillum* cultures, differing from the other small bacterium and fungus cultures, reach a size of about 3 mm.

The *Azospirillum* sp. cultures, when exponentially growing in the liquid MM and Nb(II) soft agar mediums of the composition given later on, show the morphology characteristic of the *Azospirillum* cells. The cells are vibroid and of S-form, and of the size 1-2×2-4 μm. For their increase, they need biotin. On the basis of microscopic observation they can quickly move. Their mobility can be attributed to their polar flagella. In their cells, these accumulate poly-beta-hydroxybutyrate grains, and carotines. The reddish discoloration can be explained by the ageing culture. To their increasing they can use organic acids, such as malic acid, lactic acid, pyroracemic acid and butanedioic acid, as well. The fixing of the nitrogen of the air takes place under microaerofil circumstances. Under extreme circumstances, such as in the case of drought, at low or high pH value, in lack of nitrogen or carbon source, the cells will be transformed into cysts, on which there is no flagellum, but which contain poly-beta-hydroxy-butyrate grains and are surrounded with capsular polysaccharide. The carbon-source utilizing spectrum of the micro-organisms is varying concerning the species: the A. Amazonense glucose+saccharose+inozitol+A. Brasilense glucose+saccharose and inozitol−, the A. Irakense utilizes the glucose (+) and the saccharose (+) but not the inozitol (−), finally the A. Lipoferum only the glucose. In nitrogen-free medium, the spectrum of carbon source utilizing is different to a larger extent, so the above four species can be distinguished. The carbon source utilizing spectrum of our isolated micro-organism partly differs from the ATCC 29.731 *A. Lipoferrum*, *A. Amazonense*, *A. Brasiliense* and *A. Irakense* neo-type (Holt, J. G. And collaborators, Bergeys Manual of Determinative Bacteriology, 9$^{th}$ edition, 1994). Contrary to the type groups, these properly increase in the presence of 3,5% natrium chloride, in soft agar (this will be described later on) their microscopic pictures are different in the various periods of the cultivation, their pigment production is more intensive for instance in potato extract agar.

Some isolated Azospirillums are near to the species *Azospirillum lipoferum*, *Azospirillum amazonense*, *Azospirillum brasilense* as well as to the species *Azospirillum irakense*, we performed the further experiments on these while selecting one of the *Azospirillum brasilense* groups.

From the above soil samples *Azotobacter* micro-organisms were isolated on Nfb(II) soft agar, with selective cultivation, then on MM and Fjodorov medium by dispersing and selecting one of our subspecies *on* the basis of its nitrogen fixing ability and stored it for further experiments. The cells of the group are pleiomorph, of coccoid form. In the presence of oxygen these move quickly. These are Gram-negative. These produce on nitrogen-free medium fluorescent, yellowish-green pigment, these properly utilise the rhamnoze and mezo-inozitol.

As it is well known, the Rhizobiums form nodules on the roots of the papilionaceae, then, getting among the vegetal cells, these directly transmit the fixed nitrogen to the plant. With the various papilionaceae different *Rhizobium* species enter into connection, with the soya bean the *Bradyrhizobium* group. Since this is the sole such *Rhizobium* species, which dies after the crop harvest, i.e. it does not remain in a large quantity in the soil, it is advisable to use this group for soil treatment. We isolated the *Bradyrhizobium* group on the 13$^{th}$ July from the soya plantation in Subasa near to Szeged-Kiskundorozsma. From the plants growing in the loess a well developing plant was selected and detached the well developed nodules from its roots. The psychrophilic variant of the micro-organism isolated as given in the example was deposited.

In our collected soil samples we searched for phosphate mobilising micro-organisms and tested the selected micro-organisms from systematic point of view. A part of the micro-organisms proved to be *Pseudomonas*, the other part proved to be *Bacillus* species.

The *Pseudomonas* are Gram-negative, aerobic cells of a thin stick form, these produce on the most media fluorescent pigment, these are saprophyte. No carotine production can be observed, these do not grow at temperatures over 40° C. On the gelatinous agars liquefaction can be seen. The glucose is utilized by our groups, the starch not. Although the variants of the fluorescence *Pseudomonas* groups are systematically in close connection, certain systematic heterogenity could be observed between our micro-organism and the type groups: our micro-organism—characteristically of the *Pseudomonas*- properly utilises the glucose, galactose, acetic acid, maltose, glycerin, and the pyroracemic acid. It does not utilize the fructose, D-arabinose, maltose, lactose, starch and inulin. Contrary to the type groups, however, these are able to grow on xylose, saccharose and to a certain extent, on sorbitol. As a sole carbon-source, they can utilize glycine.

On the basis of the above, one of our micro-organisms was identified as the species *Pseudomonas* fluorescent and found it standing near to the variants belonging to Biovar III group. We named the group as *Pseudomonas* fluorescent ssp.

On the basis of the systematic characters, out of the *Bacillus* cells, which can solve the insoluble phosphate, some proved to be *Bacillus polymyxa*, some proved to be *Bacillus megaterium*. Some groups were selected for further experiments.

From the potassium minerals, for the isolation of the micro-organisms capable of mobilising the potassium ion, micro-organisms from the surface of minerals containing potassium, feldspar, and muscovite were isolated, then tested as given in the examples, on solid, potassium-free media, to prove the potassium mobilisation. Applying the procedure given in the examples, by means of mutation treatments a micro-organism identified as *Streptomyces* psychrophilic was produced and deposited.

We isolated such a micro-organism, as well, which after the systematic, morphologic and ribosomal DNS tests proved to be *Micrococcus roseus* and showed an extraordinary advantageous effect in the course of the vegetal tests. One of the groups of this micro-organism Was deposited, which group had been transformed in laboratory.

The invention is also based on the fact that the micro-organisms of favorable effect, planted in the soil, can multiply as fast as possible at the time of the initial development of the sowings and the plants, under the climatic conditions in the autumn and early spring and in countries of colder climate, as well. Therefore the micro-organisms were treated, isolated and maintained according to the above as given in the example No. 4. By recognised procedures, the mutants and variants increasing at low temperatures were isolated, as well, then deposited in the National Selection of Agricultural and Industrial Micro-organisms.

The invention refers to such preparations and procedures, by applying which the yield of the vegetable cultures is increasing. The production is accompanied by cultivating the micro-organisms isolated and tested from the various arable lands, from the environment of various plants, existing in the environment of the given plant family for a long time, propagating at low temperatures, in various soils, as well, and bringing the preparation containing the culture on the relevant plants, on the seeds, or in the arable land of these. According to the invention, the preparations can be used by treating the soil, the plants or the vegetable seeds with a preparation, which contains at least one of the following micro-organisms: *Azospirillum brasilense* ssp. SW51 (NCAIM /P/ B 001293), *Azotobacter* vinelandii ssp. M657 (NCAIM /P/ B 001292), *Pseudomonas* fluorescent var. SW11 (NCAIM /P/ B 001296), *Bacillus polymyxa* var. SW17 (NCAIM /P/ B 001295/, *Bacillus megaterium* var. M326 (NCAIM /P/ B 001291), *Micrococcus roseus* ssp. A21 (NCAIM /P/ B 001294/, *Bradyrhizobium japonicum* var. PH25 (NCAIM /P/ P 0012./ and *Streptomyces albus* var. 0003 LP (NCAIM /P/ B 0012./.

As a result of the treatment the development of the plants will be accelerated, these will be more resistant to pathogens, the water supply of the soil structure and the plants will be improved and high yields are provided even with reduced use of fertilizer or non-use of any fertilizer at all.

It is one of the most important advantages of the procedure according to the invention that by the implementation thereof, in the course of the plant cultivation, the application of the nitrogen-, phosphate- and potassium-based fertilizers will be practically unnecessary or it can be reduced to a considerable extent. The environmental pollution effect of the fertilizers is evident. The compounds biosythetizing in the micro-organism cells, promoting the vegetal development accelerate the development of the treated plant, the root development and at the same time with this the water supply of the plants will be improved, the fed micro-organisms repress the development of the phytopathogenic micro-organisms, the polysaccharides biosynthetizing in the cells of some of our micro-organisms improve the soil structure, the water balance and the soil life especially favourably. The preparations according to the invention, their making and application, contrary to the known preparations and preparing procedures of the same purpose and application, are based on the use of micro-organisms of various, different effects, isolated from various soils, exerting a specific effect on a given, economically important cultivated plant, which micro-organisms can multiply at the low temperatures in the autumn and early spring and on areas of colder climate, as well.

The micro-organisms according to the invention can be cultivated on medium containing as carbon source for instance glucose, starch, saccharose, or molasses, as nitrogen source corn steep liquor, casein, yeast extract or ammonium salts, further other inorganic salts and salts dissociating on the ions of trace elements, but, as it is evident for the specialists, any assimilable carbon- and nitrogen sources, inorganic salts can be used which make possible the propagation of the bacteria according to the invention.

The culture containing the micro-organisms according to the invention can be added directly to the soil to be treated or to the plants in the medium used for the cultivation, but preparations keeping the biotic potential of the micro-organism, among these the preparation containing carriers fixing the bacteria to the seeds with adhesion forces may be prepared, too. The bacterium quantity brought to the soil may vary between $5 \times 10^{11}$ and $5 \times 10^{15}$ cells pro hectare, the favourable cell quantity is between $10^{12}$ and $10^{13}$.

In sense of Budapest Agreement, we deposited the micro-organisms isolated, identified from various vegetable environments, which can multiply at low temperatures, too, in the National Collection of Agricultural and Industrial Micro-organisms, where these are registered under the following deposit numbers:

*Azospirillum brasilense* ssp. SW51 (NCAIM /P/ B 001293),

*Azotobacter vinelandii* ssp. M657 (NCAIM /P/ B 001292),

*Pseudomonas fluorescens* var. SW 11(NCAIM /P/ B 001296),

*Bacillus polymyxa* var. SW17 (NCAIM /P/ B 001295/,

*Bacillus megaterium* var. M326 (NCAIM /P/ B 001291),

*Micrococcus roseus* ssp. A21 (NCAIM /P/ B 001294/,

*Bradyrhizobium japonicum* var. PH25 (NCAIM /P/ B 001302/ès

*Streptomyces albus* var. 0003 LP (NCAIM /P/ B 001301/.

The scope of protection also extends to the deposited groups and to their artificial and natural mutants, variants or to the group lines of the above micro-organisms gained in any known manner, as well.

*Azospirillum brasilense* ssp. SW51 (accession number NCAIM /P/ B 001293), *Azotobacter vinelandii* ssp. M657 (accession number NCAIM /P/B 001292), *Pseudomonas fluorescens* var. SW11 (accession number NCAIM /P/ B 001296), *Bacillus polymyxa* var. SW17 (accession number NCAIM /P/ B 001295), *Bacillus megaterium* var. M326 (accession number NCAIM /P/ B 001291), and *Micrococcus roseus* ssp. A21 (accession number NCAIM /P/B 001294) were deposited with National Collection of Agriculture and Industrial Microorganisms, Budapest Somlói út 14-16, 1118, Hungary, on Dec. 11, 2000. *Streptomyces albus* var. 0003 LP (accession number NCAIM /P/ B 001301) was deposited with National Collection of Agriculture and Industrial Microorganisms, Budapest Somlói út 14-16, 1118, Hungary, on May 24, 2001. The subject strains have been deposited under conditions that assure that access to the cultures will be available during the pendency of this patent application to one determined by the Commissioner of Patents and Trademarks to be entitled thereto under 37 CFR 1.14 and 35 U.S.C. 122. The deposit will be available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject deposits will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least thirty (30) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

Hereunder we illustrate the invention with examples, without limiting the scope of protection to them.

In the examples the percentages are expressed in weight percentages, unless specified otherwise.

BEST MODE OF CARRYING OUT THE INVENTION

Example No. 1

Isolation of the Micro-Organisms Fixing the Nitrogen of the Air from Various Soils and from the Environment of Various Plants and Proving of their Nitrogen Fixing Capacity The *Azospirillum* species are the bacteria of Gram-negative-variable coloration, which are able to reduce the nitrogen of the air to ammonia under microaerofil circumstances (in the presence of 1-2% oxygen) and to make available these for the plants.

*Azospirillum* species were isolated from various soil samples (humous, loess, sodic, brown and black soil, etc.), from the root environment of various plants (cereals, sunflower, corn, grasses, etc.). The chemical attractants, such as the organic acids and sugars, attract the *Azospirillum* groups by chemotaxis. Helped by their flagella, the bacteria move towards the roots and having reached them, colonise.

From the 10-, 100-, 1.000- and 10.000-fold dilutions of the given soil sample made with sterile, distilled water, 100-100 μl suspension were spread on Petri-dishes containing MM and Nfb(II) soft agar. The composition of the MM medium is as follows:

| | |
|---|---|
| $K_2HPO_4$ | 1.65 g/l |
| $KH_2PO_4$ | 0.87 g/l |
| $MgSO_4 \times 7H_2O$ | 0.29 g/l |
| NaCl | 0.18 g/l |
| $CaCl_2 \times 2H_2O$ | 0.07 g/l |
| $FeCl_3 \times 6H_2O$ | 0.01 g/l |
| $NaMoO_4 \times 2H_2O$ | 0.005 g/l |
| $MnSO_4 \times H_2O$ | 0.00014 g/l |
| $ZnSO_4 \times 7H_2O$ | 0.007 g/l |
| $CuSO_4 \times 5H_2O$ | 0.000125 g/l |
| $CoSO_4 \times 7H_2O$ | 0.00014 g/l |
| $H_3BO_3$ | 0.00003 g/l |
| Glucose | 5.0 g/l |
| Saccharose | 5.0 g/l |
| Bacto agar | 20.0 g/l |

The glucose was sterilised separately from the other components of the MM medium with autoclave (121° 0C., 30 minutes), then mixed therewith after cooling down to the temperature of 60° C. The sterile medium was adjusted to pH: 7.4 with a sterile 1N NaOH solution.

| | |
|---|---|
| L-malic acid | 5.0 g |
| Dipotassium-hydrogen-phosphate | 0.5 g |
| Magnesium-sulphate × 7water | 0.2 g |
| Sodium-chloride | 0.1 g |
| Calcium-chloride | 0.02 g |
| Trace element solution* | 2.0 ml |
| Brom thymol blue (water solution of 0.5% of material solved in 0.2 N KOH) | 2.0 ml |
| Solution of 1.564% of Fe-EDTA | 4.0 ml |
| Vitamin solution** | 1.0 ml |
| Agar | 1.75 g |

The medium was adjusted with 1N water KOH solution to pH: 6.8.

*Composition of the trace element solution is as follows:

| | |
|---|---|
| Ferro-II-sulphate × 7 $H_2O$ | 200 mg |
| Ferro-III-chloride × 6 $H_2O$ | 10 mg |
| Manganese sulphate × $H_2O$ | 1 mg |
| Cupric sulphate × 5 $H_2O$ | 2 mg |
| $NaMoO_4$ × 2 $H_2O$ | 1 mg |
| Cobalt-chloride × 6 $H_2O$ | 2 mg |
| Zinc-sulphate × 7 $H_2O$ | 2 mg |
| Sodium-tetraborate × 10 $H_2O$ | 1 mg |
| $P_2O_5$ × 24 $WO_3$ × $H_2O$ | 0.5 mg |
| Bismuth-nitrate × 5 $H_2O$ | 0.1 mg |
| Tin-chloride | 0.01 mg |
| Selenium chloride | 0.01 mg |
| Potassium iodide | 1 mg |
| Citric acid | 100 mg |
| Distilled water | 1000 ml |

**Composition of the vitamin solution is as follows:

| | |
|---|---|
| C vitamin | 50 mg |
| B1 vitamin | 5 mg |
| E vitamin | 2 mg |
| A vitamin | 2 mg |
| Biotin | 4 mg |
| Distilled water | 100 ml |

The bacteria brought in the media to be found on the MM plates were placed in anaerobe thermostats, by exchanging the air space of the thermostat for nitrogen, then set to oxygen concentration of 1,6% with the reflux of air of satisfactory quantity. the plates were incubated at a temperature of 32° C., then after 72 hours the *Azospirillum* organisms were identified. Corresponding to the dilution line, on the plate spread with the 10-fold diluted suspension a continuous bacterium field has developed, whilst from the 10.000-fold diluted suspension generally 30-50 cultures have developed. The *Azospirillum* cultures, differing from the other small bacteria, and the fungus cultures, reached a size of about 3 mm. Out of the cultures, several ones were morphologically similar to the *Azospirillum* cultures. Out of these we further studied some ones.

The Nfb(II) soft agar cultures were placed in aerobe thermostat, in the above medium and under the above cultivating circumstances, first of all the *Azospirillums* multiply, and with recognisable, characteristic morphology.

the various *Azospirillum* bacterium groups gained from the MM and Nfb(II) media were grown in compliance with the microbiological practice, in such a manner that the primary bacterium culture was spread two times on one culture, on a complete Tag medium. The *Azospirillum* bacterium groups were purified by spreading two times on one culture in liquid Tag medium and stored in the group culture. The bacterium suspension at the temperature of −80° C. was considered as the group culture and all the experiments were started from this culture.

| | |
|---|---|
| Bacto trypton (Difco) | 1.0% |
| Yeast extract (Difco) | 0.1% |
| NaCl | 0.5% |
| Agar | 2.5% |

After sterilization, the water solutions of the following compounds, in the following final concentration were added:

0.1%0.1 M $CaCl_2 \times 6H_2O$
0.1%0.1 M $MgCl_2 \times 6H_2O$
0.2% glucose (separately sterilised)

After the sterilisation th pH of the medium was adjusted to 7.0-7.2.

The root colonisation can be detected by a simple experiment. On the root of corn and wheat plant treated with *Azospirillum* bacterium, sown in sterile perlite (pot of diameter of 15 cm) and cells of equal number ($1 \times 10^{10}$ cells pro pot), on the basis of microscopic counting, essentially more *Azospirillum* cells were to be detected, than in the controls. The root colonisation takes place on the basis of a specific recognition mechanism. In the course of the colonisation, the *Azospirillum* cells penetrate in the matrix of the root and these there—by means of their active nitrogen fixing—can cover a part of the nitrogen need of the main plant (associative nitrogen fixing). This was proved by the growth of higher green mass of corn and wheat inoculated with *Azospirillum* groups in the course of our laboratory experiments, the results of which is detailed later on. The *Azospirillums* produce vegetable hormones and materials promoting the growth, as well. the rise of these materials and their favourable effect on the main plant can be shown with the increased germinating efficiency and with the more intensive plant growth, with experiments performed under laboratory circumstances.

The morphological characteristics of the isolated *Azospirillum* species are found in the general part of the description.

On Nfb(II) soft agar with selective cultivation, than in nitrogen-free MM medium with selective cultivation, *Azospirillum* micro-organisms were isolated from ploughland soil samples. These groups were found to be *Azospirillum brasilense* according to the systematic characteristics and the carbon-source utilisation spectrum, fixing the molecular nitrogen of the air to a large extent with SW5-01-07, then, as described later on, variants multiplying at low temperatures as well, biosynthetizing polysaccharide were isolated, and one of these deposited.

For the isolation of the *Azotobacter* groups, in addition to the use of the Nfb(II) and MM media of the composition given above, the soil samples were cultivated in Fjodorov medium, too, where the Azotobacters show characteristic morphological properties. Composition of the Fjodorov medium is as follows:

| | |
|---|---|
| Potassium dihydrogen-phosphate | 0.03% |
| Calcium-hydrogen-phosphate | 0.02% |
| Potassium-sulphate | 0.02% |
| Magnesium-sulphate × 7 aqv. | 0.03% |
| Calcium-carbonate | 0.5% |
| Sodium-chloride | 0.05% |
| Ferric/III/-chloride | 0.02% |
| Sodium-molybdenate | 0.0002% |
| Mannitol | 2.0% |
| Bacto agar | 2.0% |

The pH of the medium prior to sterilisation was adjusted with 1N sodium-hydroxide solution to 7.0.

On Nfb(II) soft agar with selective cultivation, then on nitrogen-free MM and Fjodorov medium with selective cultivation, *Azotobacter* micro-organisms were isolated from plough-land soil samples. These groups were found to be *Azotobacter vinelandii* according to the systematic characters and the carbon source utilisation spectrum, fixing the molecular nitrogen of the air to a large extent with the mark M65-01-34, then, as described later on, variants multiplying at a low temperature were isolated, as well and one of these deposited by us.

The nitrogen fixing capacity of the *Azospirillum* and *Azobacter* groups was determined by the acetylene reduction method, too. According to the method (Dilworth M. J., J. Biochem. Biophys. Acta, 27, 285,1996), acetylene was injected in the culture in a closed dish with an injector, then, after incubation of 12 hours, 0.25 ml gas mixture was injected in the Propak N column of the Perkin-Elmer gas chromatograph. The acetylene and ethylene concentration of the gas mixture were determined by a hydrogen flame ionisation detector. From the height of the acetylene and ethylene peaks it could definitely be concluded on the enzyme complex activity of the nitrogenase. Our *Azospirillum* and *Atzotobacter* groups reduced, within 1 hour, acetylene of a quantity between 15 and 85 nmol to ethylene.

The *Bradyrhizobium* group was isolated on the 13 Jul. 2000 from the soya plants of Subasa located near to Szeged-Kiskundorozsma. From the plants growing in the loess a well developing plant was selected and from its roots the well developed nodules were removed. the nodules with sterile, distilled water were washed, squashed, then the particles were suspended in physiologic salt solution. From the suspension, under sterile conditions, dilution series were prepared and spread on complete medium. The nitrogen fixing capacity of the cultures growing after the incubation of 48 hours by a so-called symbiotic plant test, was determined as follows: the surface of commercial medic (*Medicago sativa*) seeds was sterilised by heat treatment of 2 hours made at a temperature of 72° C. and by careful rinsing with a Hypo solution of 20%, then germinated in a distilled water medium containing 1% agar. The seedlings were placed on 1,5% Gibson oblique agar (see later on) and raised in greenhouse for a week. The one week old plants were inoculated with the cells of a bacterium culture each and raised in greenhouse for further eight weeks. From the groups belonging to the three plants showing a prominently optimal development (dry-weight of the parts over the root 22-26 mg, contrary to the weight of the control plants of 3-5 mg) three were selected and on the basis of their properties being important from morphologic and systematic point of view, we named them *Bradyrhizobium japonicum* var. PH-2-1-3.

Example No. 2

Isolation of Phosphate- and Potassium Solubilizing Micro-Organisms

Soil samples were collected in various parts of the world, the water suspensions of the samples spread on Tag medium (see above), then the isolated materials of *Pseudomonas* and *Bacillus* culture and cell morphology were tested.

The various *Pseudomonas* and *Bacillus* groups were purified in compliance with the microbiological practice by spreading the primary bacterium culture several times on a single culture, on a complete TAg medium. The bacterium groups were increased and stored purified with spreading in liquid and solid TAg medium.

The phosphate mobilising properties of the micro-organisms were tested in a Nutrient Agar (Oxoid) medium containing 1% hydroxi-apatite, completed with modified Pikovskaya (HP) and 10% tricalcium-phosphate and glucose (0,2%).

Composition of the media used in the course of the experiments is as follows:

| modified Pikovskaya medium: | |
| --- | --- |
| Hydroxi-apatite | 1.0% |
| $(NH_4)_2SO_4$ | 0.05% |
| NaCl | 0.02% |
| KCl | 0.02% |
| $MgSO_4 \times 7H_2O$ | 0.01% |
| Yeast extract | 0.05% |
| Agar | 1.5% |
| Glucose (separately serilised) | 1.0% |

The solutions of the following compounds were added to the medium after sterilisation:

1% 20 mg/100 ml $FeSO_4 \times 7H_2O$

1% 40 mg/100 ml $MnSO_4 \times H_2O$

Prior to the sterilisation the medium was adjusted to pH: 7.2.

Naoxg: Nutrient agar (Oxoid) prepared according to the instructions of the manufacturer+0.2% glucose.

During testing the phosphate solubilizing capacity of the groups selected in the course of the preliminary experiments in Pikovskaya (HP) medium, the cultures grown within 3-4 days at a temperature of 30° C. produced solution rings of 29 and 38 mm. The cell suspensions of the same groups obtained from TAg oblique agar, with 1 ml distilled water were dropped in holes made on Naoxg plates completed with 10% tricalcium-phosphate (0.1 ml/hole). Incubating the cultures at a temperature of 30° C., within 2-3 days well visible solution rings can be observed. The size of these was 24 mm when using the *Pseudomonas* groups tested in detail, and 26 mm when we used the *Bacillus* groups, the average size amounted to 34 mm.

Each individual *Pseudomonas* group and some *Bacillus* groups proved to have intensive phosphate solubilising properties. The groups carry both inorganic phosphate variants well detectable in solution, so it can be stated that these have excellent phosphate solubilising properties.

On basis of their systematic characteristics and the carbon utilisation spectrum, The fourteen *Pseudomonas* and twenty-five *Bacillus* micro-organisms selected on the basis of the tests were found to be *Pseudomonas fluorescens* and *Bacillus polymyxa* as well as *Bacillus megaterium*, which were marked in the following sequence of order: SW1-1-14, SW17-1-15 and M32-1-10, then, as given later on, variants multiplying at low temperature, as well and biosynthetizing polysaccharide in large quantities were isolated and deposited.

isolation of the micro-organisms mobilizing the potassium ions was accomplished as described above, with the difference of excluding the potassium chloride from the Pikovskaya (HP) medium of the composition given above and adding 1% feldspar crushed in fine powder and mica schist instead of the hydroxy-apatite.

In the surrounding of the micro-organism cultures bringing the minerals insoluble in water completely or partly in solution, a transparent zone will be formed.

Some of these were selected and on the basis of the systematic characteristics, morphologic properties and the carbon source utilization spectrum were found to be *Bacillus* and *Streptomyces*, our 15 groups were marked as No. 1-015-0003, and then, as described later on, variants multiplying at low temperature were isolated, too and one of these had been deposited.

Example No. 3

Isolation of Microorganisms Producing Siderophores and Vegetable Hormones

The siderephore and hormone production capacity of the groups isolated as described in examples No. 1 and 2 were tested by using King B medium. The composition of this is as follows:

| Peptone | 2% |
| --- | --- |
| Glycerin | 1% |
| $K_2HPO_4$ | 0.15% |
| $MgSO_4 \times 7H_2O$ | 0.15% |
| Agar | 2% |

Prior to sterilisation, the medium was adjusted to pH: 7.2 with sodium-hydroxide solution.

The *Pseudomonas* groups producing the siderophores fix the iron-ions, which they transmit to the plant in iron-poor soil, as well. Moreover, these inhibit the propagation of some phytopathogenic micro-organisms, such as the *Erwinia caratovora*, since these cannot utilize the fixed iron. We tested the siderophore production by inhibiting the growth of the *Escherichia coli* MC1061 group. The cell suspensions of the two groups from agar culture were prepared with distilled water, then cultivated dropping on iron-free and iron-containing (1 µM $FeCl_3 \times 7H_2O$) King B plate (30-50 µl) for 48 hours, at a temperature of 28° C., followed by spraying the plate with *E. Coli* MC1061 culture obtained from TAg agar and continuing the incubation for further 28 hours, at the temperature of 28° C. Around the cultures, various inhibition zones can be observed. the results of the average of four experiments are shown on Table No. 1. as negative control *Bacillus megaterium*, as positive control *Pseudomonas fluorescens*(were used).

TABLE NO. 1

| Micro-organism□King B inhibition zone□King B + 1 µM $FeCl_3$ Inhibition zone□□SW1-1-6. |
| --- |
| SW1-1-12 |
| P. fluores. |
| B. megater.□++++ |
| ++ |
| + |
| □- |
| - |
| - |

□□*Extent of inhibition:
− no,
+ low,
++ and +++ high and very high

In the course of the testing of the siderophore production with the mob4 and positive control group a considerable inhibition zone was observed, which ceased in the presence of iron ions.

As mentioned before, some *Pseudomonas* groups produce vegetal hormones. Selected micro-organisms were tested whether these are capable of the biosynthesis of ghibberellic-acid in the TAg medium of the composition given above. The tests were performed by using ghibberellic acid A standard (Sigma), by (40 µg/ml) silica gel (Merck) thin layer chromatography. extraction of the cultures with ethyl-acetate, was followed by an extraction with sodium-hydroxide-carbonate of double volume, then in a solution of pH:2.5 with ethyl-acetate again. In the evaporation residue of the extract the following groups a spot of $R_f$ value near to the standard were found:

TABLE NO. 2

| Group | $R_f$ | Size of the spot (mm$^2$) |
|---|---|---|
| Standard | 0.41 | 24 |
| SW1-1-6 | 0.46 | 17 |
| M32-1-9 | 0.42 | 27 |
| P. fluor. | 0.49 | 14 |
| B. megat. | 0.57 | 7 |

The groups marked SW1-1-6 and M32-1-9 were selected (these produce approximately 3-15 µg hormone pro millimeter).

The groups as described in the general part were tested and identified from systematic point of view.

Example No. 4

Isolation of Micro-Organisms Producing Extracellular Polysaccharide

4A. Selection of the *Bradyrhizobiums*

The *Bradyrhizobium* PH2-1-3 groups were spread in Tag medium containing 1% glucose and 1% saccharose (see above) and tested polysaccharide (slime) quantity around the cultures. The PH2-1-1 and -2 groups biosynthetizing the polysaccharide were selected.

4B. Isolation of *Bacillus*

The *Bacillus* M32-1-10 and SW17-1-15 groups were spread in Tag medium containing 1% glucose and 1% saccharose (see above) and tested the polysaccharide (slime) quantity around the cultures. The M32-1-6, 8 and 10 and the SW17-1-7, 11 and 15 groups biosynthetising the polysaccharide were selected.

The isolated micro-organism proved to be *Micrococcus roseus*, on complete medium containing glucose and saccharose is biosynthetising large quantities of polysaccharide transforming the culture-medium into a viscous material.

The selected groups, according to our tests, are biosynthetizing water-soluble polysaccharide of succionoglucone-type, of known structure.

Example No. 5

Isolation of Cold-Enduring Micro-Organisms

The micro-organisms selected according to the examples 1-4. were treated with agent causing mutations and with radiation. The suspensions of the micro-organisms prepared with distilled water were treated with 0.01, 0.1, 1.0, 10 and 100 µg/ml nitroso-guanidine for 1, 3, 5, 10 and 30 minutes. Following the treatment, the cell suspension was centrifuged, washed with distilled water two times, then the cells spread on TAg culture medium. the treatment with was repeated distilled water cell suspension containing $10^9$ micro-organisms pro millimeter, by keeping the cells for 1, 3, 5, 10 and 30 minutes under a 15 W UV lamp, in a distance of 10 cm therefrom. the cell suspensions were spread on Tag culture medium, with serial dilution.

The TAg cultures were incubated at a temperature of 18° C. for 192 hours, followed by isolating the biggest cultures on TAg oblique agars incubated at a temperature of 18° C.

The following grown cultures are controlled and maintained.

Out of the isolated, selected and cold-enduring micro-organisms were separated and deposited:

*Azospirillum brasilense* ssp. SW51 (NCAIM /P/ B 001293),

*Azotobacter vinelandii* ssp. M657 NCAIM /P/ B 001292),

*Pseudomonas fluorescens* var. SW11 (NCAIM /P/ B 001296),

*Bacillus polymyxa* var. SW17 (NCAIM /P/ B 001295/,

*Bacillus megaterium* var. M326 (NCAIM /P/ B 001291),

*Micrococcus roseus* ssp. A21 (NCAIM /P/ B 001294/,

*Bradyrhizobium japonicum* var. PH25 (NCAIM /P/ B 001302/es

*Streptomyces albus* var. 0003 LP (NCAIM /P/ B 001301/.

Example No. 6

Cultivation of Micro-Organisms

6A. Cultivation on Complete Culture Medium:

From the TAg culture medium oblique agar cultures were prepared, then incubated at a temperature of 30° C., for 48 hours. From the *Azospirillum, Azotobacter, Bacillus, Bradyrhizobium, Pseudomonas, Streptomyces* or *Micrococcus* cultures were inoculated in the culture mediums marked—Ta1i—of the following composition:

| | |
|---|---|
| Gllucose (separately sterilised in 50% water solution) | 0.5% |
| Molasses | 1.5% |
| Corn steep liquor (50% dry substance) | 1.5% |
| Gistex yeast extract | 0.2% |
| Acid casein | 0.1% |
| Ammonium-sulphate | 0.1% |
| Ammonium-nitrate | 0.1% |
| Calcium-carbonate | 0.3% |
| Potassium-dyhidrogen-phosphate | 0.1% |
| Sodium-chloride | 0.1% |
| Magnesium-sulphate × 7 H$_2$O | 0.1% |
| Palm oil | 0.2% |

The 100-100 ml portions of the culture medium were filled in 500 ml Erlenmeyer-flasks, then sterilized at a temperature of 121° C., for 30 minutes. the sterile culture media were inoculated with the micro-organisms grown on the oblique agar cultures and the cultivation of the cultures was carried out at a temperature of 25° C., on a rotating table working with 260 circular rotations pro minute, for 36 minutes. The growth was observed with microscopic test, then, using a quantity of 5% from the inoculums, which were inoculated in the Ta1f principal fermentation culture mediums of the following composition:

| | |
|---|---|
| Glucose (separately sterilised in 50% water solution) | 1.5% |
| Molasses | 2.5% |
| Corn steep liquor (50% dry substance) | 1.5% |
| Gistex yeast extract | 0.4% |
| Acid casein | 0.4% |
| Ammonium sulphate | 0.2% |
| Ammonium-nitrate | 0.2% |
| Calcium-carbonate | 0.3% |
| Potassium-dihydrogen-phosphate | 0.2% |
| Sodium-chloride | 0.1% |

-continued

| | |
|---|---|
| Magnesium-sulphate × 7 H$_2$O | 0.2% |
| Trace element solution* | 0.45% |
| Palm oil | 0.2% |

*Composition of the trace element solution is according to example No. 1.

The culture media pro 100 ml in Erlenmeyer-flasks were sterilized, and in laboratory fermenters of a gross volume of 10 l and of a net volume of 5 l, under the circumstances given above.

The cultures placed in the flasks were cultivated on rotation table, while in the fermenters in the usual manner, by v/v airing and by operating a turbo mixer with double inlet, rotating 360 times pro minute, for 24 hours, when the cell number pro millimeter—depending on the bacterium—reaches the values $4 \times 10^8 - 1.3 \times 10^9$.

For the preparation of cultures of larger quantities, 10 liters cultures were prepared on the Ta1i culture medium of the composition given above, under the aforesaid fermentation conditions, then 100 liters sterilized Ta1i and 100 liters Ta1f culture medium were inoculated with 5-5 liters each. The cultivation was continued for 24 hours, under the above fermentation circumstances, then the culture grown on the Ta1f culture medium in the soil, 50 liters of the culture grown on the Ta1i culture medium was used to inoculate 1000 liters of sterilized Ta1f culture medium. the cultivation was carried out under the above fermentation circumstances for 24 hours, then, followed the inspection, the culture was ready for use. In the case of an unusually intensive foaming, 0.01% polypropylene-glycol as antifoaming agent was added.

6B. Cultivation on Semi-Minimal Culture Medium:

the procedure given in example No. 6 was repeated with the difference that instead of the Ta1f culture medium the Ta2f culture medium of the following composition was used:

| | |
|---|---|
| Glucose (sterilised separately in 50% water solution) | 1.5% |
| Molasses | 0.5% |
| Acid casein | 0.1% |
| Ammonium-sulphate | 0.7% |
| Ammonium-nitrate | 0.5% |
| Calcium-carbonate | 0.3% |
| Potassium-dihydrogen-phosphate | 0.3% |
| Sodium-chloride | 0.1% |
| Magnesium-sulphate × 7 H$_2$O | 0.2% |
| Trace element solution* | 0.35% |
| Palm oil | 0.2% |

*The composition of the trace element solution is in conformity with that in example No. 1.

After completion of the cultivations, the cultures contain, depending on the bacterium, $1-7 \times 10^8$ cells pro milliliter.

Example No. 7

Improvement of the Soil Structure and Plant Cultivation Experiments

7A. Experiments for the Improvement of the Soil Structures

Sandy soil collected at the Danube, near to Somlyòsziget and the clay soils from Esztergom were placed in trays of 90×90 cm, the layer thickness was 25 cm. The sand soil was treated with 10 g ammonium-nitrate and 5 g calcium-phosphate pro tray. Corn was sown in the tray, with 104 seeds pro tray. At the evaluation we have not taken the data of the five biggest and the five most underdeveloped plants. The weight of the roots washed with distilled water following a desiccation of two days, at a temperature of 45° C. were measured. Tray No. 1 was abundantly watered, tray No. 2 at sowing abundantly watered but not at all later on. The trays marked "a", were inoculated with as micro-organisms biosynthetising the polysaccharides the cultures of the micro-organism groups *Bacillus polymyxa* var. SW17 (NCAIM /P/ B 001295/, *Bacillus megaterium* var. M326 (NCAIM /P/ B 001291), *Micrococcus roseus* ssp. A21 (NCAIM /P/ B 001294/and *Bradyrhizobium japonicum* var. PH25 (NCAIM /P/ B 001302/, deposited in the National Collection of the Agricultural and Industrial Micro-organisms, prepared according to example No. 6., with $10^8$ cells for one square meter from each bacterium. The "b"-marked trays were not treated with micro-organisms.

In Table No. 3, the results obtained on the $33^{rd}$ day following the sowing are shown. The results are expressed with the average values counted for one plant.

TABLE No. 3

| Soil | Tray | Treatment | Height of the plant (cm) | Weight of the root system (mg) |
|---|---|---|---|---|
| Sandy | No. 1 | A | 24 | 945 |
|  |  | B | 17 | 634 |
|  | No. 2 | A | 18 | 866 |
|  |  | B | 11 | 757 |
| Clay | No. 1 | A | 27 | 1095 |
|  |  | B | 23 | 1213 |
|  | No. 2 | A | 20 | 1012 |
|  |  | B | 19 | 689 |

In table No. 4. the extent of crumbling and cracking of the not watered sandy and clay soils (trays No. 2) is shown. By the extent of crumbling we mean that the majority of the soil fragments scattered on a paper sheet and not disintegrating in the course of a slight shaking is of a size below 2 mm (−), between 2-5 mm (+), or over 5 mm (++). the extent of cracking of the soil surface is marked so that lack of cracks is marked ++, the slight haircracks are marked +, whilst the presence of the big lines of break, cracks characteristic of the droughty soils is marked −.

TABLE NO. 4

| Soil | Treatment | Extent of crumbling | Extent of cracking |
|---|---|---|---|
| Sandy | A | + | + |
|  | B | − | − or + |
| Clay | A | ++ | + |
|  | B | ++ | ++ |

It can be seen from the data of Tables No. 3. and 4. that the presence of the micro-organisms biosynthetizing the polysaccharides improves the development of the plants and the favorable soil structure.

7B. Field Experiments

Experiments were performed at the Improvement and Cultivation Technological Station of Mosonmagyarovar University, in 2000, in random block arrangements repeated four times, with 10 liters of micro-organism mixture pro hectare.

Type of the experimental soil: Danube-region, thickness: 120-140 cm, humus contents 2.4%, rainfall: poor.

SPRING WHEAT

Protein-content %

| | |
|---|---|
| Control | 11.80 |
| NPK 200 kg/ha | 11.87 |
| BactoFil A | 11.96 |

Protein-content corr. to dry substance %

| | |
|---|---|
| Control | 13.84 |
| NPK 200 kg/ha | 13.91 |
| BactoFil A | 14.00 |

Wet gluten %

| | |
|---|---|
| Control | 32.0 |
| NPK 200 kg/ha | 31.1 |
| BactoFil A | 31.1 |

Thousand grains weight (g)

| | |
|---|---|
| Control | 36.4 |
| NPK 200 kg/ha | 36.8 |
| BactoFil A | 36.4 |

Grinding %

| | |
|---|---|
| Control | 50.5 |
| NPK 200 kg/ha | 50.0 |
| BactoFil A | 49.8 |

Falling number (sec)

| | |
|---|---|
| Control | 278.3 |
| NPK 200 kg/ha | 281.5 |
| BactoFil A | 272.5 |

Gluten-flattening (cm)

| | |
|---|---|
| Control | 2.75 |
| NPK 200 kg/ha | 3.25 |
| BactoFil A | 2.75 |

Gluten-stretching (cm)

| | |
|---|---|
| Control | 12.5 |
| NPK 200 kg/ha | 11.8 |
| BactoFil A | 12.3 |

Zeleny-index

| | |
|---|---|
| Control | 30.0 |
| NPK 200 kg/ha | 30.3 |
| BactoFil A | 30.8 |

Valorigraph water-absorbing capacity (ml)

| | |
|---|---|
| Control | 31.3 |
| NPK 200 kg/ha | 31.6 |
| BactoFil A | 31.4 |

Valorigraph value

| | |
|---|---|
| Control | 57.3 |
| NPK 200 kg/ha | 53.1 |
| BactoFil A | 48.0 |

Bulk of loaf (cm³)

| | |
|---|---|
| Control | 962.5 |
| NPK 200 kg/ha | 977.5 |
| BactoFil A | 1055.0 |

-continued

SPRING WHEAT

Morphological ratio of bread

| | |
|---|---|
| Control | 2.38 |
| NPK 200 kg/ha | 2.46 |
| BactoFil A | 2.32 |

Protein-yield (kg/ha)

| | |
|---|---|
| Control | 469.8 |
| NPK 200 kg/ha | 498.6 |
| BactoFil A | 510.3 |

Plant height (cm)

| | |
|---|---|
| Control | 56.3 |
| NPK 200 kg/ha | 57.7 |
| BactoFil A | 55.4 | grain crop

| | t/ha | Control % |
|---|---|---|

Grain crop counted for 13% moisture (g/parcel)

| | | |
|---|---|---|
| Control | 3.366 | 100.0 |
| NPK 200 kg/ha | 3.552 | 105.5 |
| BactoFil A | 3.617 | 107.5 |

Grain crop (g/parcel)

| | | |
|---|---|---|
| Control | 3.398 | 100.0 |
| NPK 200 kg/ha | 3.584 | 105.5 |
| BactoFil A | 3.646 | 107.3 |

Moisture content at harvest %

| | |
|---|---|
| Control | 14.08 |
| NPK 200 kg/ha | 14.00 |
| BactoFil A | 13.93 |

Test weight (kg)

| | |
|---|---|
| Control | 69.8 |
| NPK 200 kg/ha | 70.4 |

CORN

Raw crop on cobs (kg/parcel)

| | Raw crop on cobs (t/ha) | Control % |
|---|---|---|
| Control | 5.725 | 100.0 |
| NPK 200 kg/ha | 6.848 | 119.6 |
| BactoFil A | 6.495 | 113.4 |

| | Grain crop (t/ha) | Control % |
|---|---|---|

Grain crop counted on 14% (kg/parcel)

| | | |
|---|---|---|
| Control | 5.496 | 100.0 |
| NPK 200 kg/ha | 6.614 | 120.3 |
| BactoFil A | 6.175 | 112.3 |

Moisture content of grain %

| | |
|---|---|
| Control | 18.40 |
| NPK 200 kg/ha | 17.78 |
| BactoFil A | 19.63 |

-continued

| CORN | | |
|---|---|---|
| | Stalk weight (t/ha) | Control % |
| Stalk weight (kg/parcel) | | |
| Control | 2.672 | 100.0 |
| NPK 200 kg/ha | 3.016 | 112.9 |
| BactoFil A | 2.886 | 108.0 |
| Moisture content of stalk % | | |
| Control | 26.1 | |
| NPK 200 kg/ha | 25.6 | |
| BactoFil A | 25.9 | |
| Stalk weight counted on 14% (kg/parcel) | | |
| Control | 2.416 | 100.0 |
| NPK 200 kg/ha | 2.740 | 113.4 |
| BactoFil A | 2.613 | 108.2 |
| Stem number (thousand pcs/ha) | | |
| Control | 38.41 | |
| NPK 200 kg/ha | 39.13 | |
| BactoFil A | 39.86 | |
| Cob number pro stem (pcs/parcel) | | |
| Control | 1.04 | |
| NPK 200 kg/ha | 1.10 | |
| BactoFil A | 1.05 | |
| Cob number (thousand pcs/ha) | | |
| Control | 39.86 | |
| NPK 200 kg/ha | 42.93 | |
| BactoFil A | 42.03 | |
| Thousand grains weight of raw grain (g) | | |
| Control | 255.2 | |
| NPK 200 kg/ha | 259.2 | |
| BactoFil A | 263.3 | |
| Thousand grains weight of grain for 14% moisture (g) | | |
| Control | 245.6 | |
| NPK 200 kg/ha | 250.9 | |
| BactoFil A | 251.0 | |
| Test weight (kg) raw | | |
| Control | 65.9 | |
| NPK 200 kg/ha | 65.1 | |
| BactoFil A | 64.6 | |
| Weight of one cob (kg) for 14% moisture | | |
| Control | 0.121 | |
| NPK 200 kg/ha | 0.136 | |
| BactoFil A | 0.131 | |
| Grain number pro cob (db) | | |
| Control | 493.5 | |
| NPK 200 kg/ha | 545.1 | |
| BactoFil A | 523.1 | |
| Moisture content of cob % | | |
| Control | 19.4 | |
| NPK 200 kg/ha | 20.7 | |
| BactoFil A | 18.9 | |
| Weight of cob (g) | | |
| Control | 22.3 | |
| NPK 200 kg/ha | 22.3 | |
| BactoFil A | 22.4 | |
| Harvest-index | | |
| Control | 44.1 | |
| NPK 200 kg/ha | 41.5 | |
| BactoFil A | 42.3 | |

| SUGAR BEET | | |
|---|---|---|
| | Beet pcs/ha | |
| Control | 79891 | |
| NPK 200 kg/ha | 81159 | |
| BactoFil B | 83696 | |
| | Crop of tops (t/ha) | Control % |
| Crop of tops (kg/parc) | | |
| Control | 13.41 | 100.0 |
| NPK 200 kg/ha | 13.96 | 104.1 |
| BactoFil B | 15.38 | 114.7 |
| Crop of roots (kg/parc) | | |
| Control | 30.46 | 100.0 |
| NPK 200 kg/ha | 36.74 | 120.6 |
| BactoFil B | 39.35 | 129.2 |
| Proportion of tops-roots | | |
| | Proportion of tops-roots | Control % |
| Control | 0.443 | 100.0 |
| NPK 200 kg/ha | 0.381 | 85.9 |
| BactoFil B | 0.391 | 88.2 |
| Average root weight (dkg) | | |
| | Average root weight (dkg) | Control % |
| Control | 38.2 | 100.0 |
| NPK 200 kg/ha | 45.3 | 118.6 |
| BactoFil B | 47.1 | 123.5 |
| | Digestion % | Control % |
| Digestion % | | |
| Control | 11.61 | 100.0 |
| NPK 200 kg/ha | 11.07 | 95.3 |
| BactoFil B | 10.59 | 91.3 |
| Na-contents (mg/100 g beet) | | |
| Control | 1.94 | |
| NPK 200 kg/ha | 2.28 | |
| BactoFil B | 2.08 | |
| Alfa-amino-N contents (mg/100 g beet) | | |
| Control | 1.20 | |
| NPK 200 kg/ha | 1.02 | |
| BactoFil B | 1.02 | |
| K-content (mg/100 g beet) | | |
| Control | 2.52 | |
| NPK 200 kg/ha | 1.89 | |
| BactoFil B | 2.10 | |
| Deduction % | | |
| Control | 2.95 | |
| NPK 200 kg/ha | 2.68 | |
| BactoFil B | 2.68 | |
| Contents of purified sugar % | | |
| | Contents of purified sugar % | Control % |
| Control | 8.66 | 100.0 |
| NPK 200 kg/ha | 8.39 | 96.9 |
| BactoFil B | 7.92 | 91.4 |

-continued

SUGAR BEET

Gross sugar yield (t/ha)

|  | Gross sugar yield (t/ha) | Control % |
|---|---|---|
| Control | 3.557 | 100.0 |
| NPK 200 kg/ha | 4.081 | 114.7 |
| BactoFil B | 4.181 | 117.5 |

|  | Net sugar yield (t/ha) | Control % |
|---|---|---|
| Control | 2.656 | 100.0 |
| NPK 200 kg/ha | 3.091 | 116.4 |
| BactoFil B | 3.125 | 117.7 |

Example No. 8

Preparation of Preparations Containing the Micro-Organisms According to the Invention 8A. Preparation of Micro-Organism Mixture:

The cultures *Azospirillum brasilense* ssp. SW51 (NCAIM /P/ B 001293), *Azotobacter vinelandii* ssp. M657 (NCAIM /P/ B 001292), *Pseudomonas fluorescens* var. SW11 (NCAIM /P/ B 001296), *Bacillus polymyxa* var. SW17 (NCAIM /P/ B 001295/, *Bacillus megaterium* var. M326 (NCAIM /P/ B 001291), *Micrococcus roseus* ssp. A21 (NCAIM /P/ B 001294/, *Bradyrhizobium japonicum* var. PH25 (NCAIM /P/ B 001302/and *Streptomyces albus* var. 0003 LP (NCAIM /P/ B 001301/prepared according to example No. 6 were mixed, optimally in equal proportions and applied in the soil to be treated, in a quantity between 5 liters and 50 liters, optimally in a quantity of 12 liters/ha, in any frost-free period of the year, optimally between March and October.

8B. Preparation for the Treatment of Monocotyledons

Following the procedure according to example No. 6. a preparation was made with the difference that the following micro-organisms were used:

*Azospirillum brasilense* ssp. SW51 (NCAIM /P/ B 001293), *Azotobacter vinelandii* ssp. M657 (NCAIM /P/ B 001292), *Pseudomonas fluorescens* var. SW1 (NCAIM /P/ B 001296), *Bacillus polymyxa* var. SW17 (NCAIM /P/ B 001295/, *Bacillus megaterium* var. M326 (NCAIM /P/ B 001291), es *Streptomyces albus* var. 0003 LP (NCAIM /P/ B 001301/.

8C. Preparation for the Treatment of Dicotyledons

Following the method according to example No. 6 with the difference that the following micro-organisms were used:

*Azospirillum brasilense* ssp. SW51 (NCAIM /P/ B 001293), *Azotobacter vinelandii* ssp. M657 (NCAIM /P/ B 001292), *Pseudomonas fluorescens* var. SW11 (NCAIM /P/ B 001296), *Bacillus polymyxa* var. SW17 (NCAIM /P/ B 001295/, *Bacillus megaterium* var. M326 (NCAIM /P/ B 001291), *Micrococcus roseus* ssp. A21 (NCAIM /P/ B 001294/, *Bradyrhizobium japonicum* var. PH25 (NCAIM /P/ B 001302/, preparation according to the invention was prepared.

8D. Making of Preparation Dried in Frozen Condition 2 liters from the water micro-organism suspension according to example No. 6 were lyophilized in a Gelman SP54 lyophilizing equipment, acting according to the instructions of use of the equipment. The dry micro-organism powder was used in itself or depending on the use, mixed with calcium-carbonate, starch, glucose, or cellulose in proportions between 1:1 and 1:100, then storing the preparation until the use, at a temperature between 4 and 10° C.

8E. Making of Preparation Containing Carrier:

Optimally equal proportion of the cultures prepared on the culture medium according to the example No. 6 were mixed with organic manure, soy flour (4 mesh general grain size), methyl-cellulose or potato starch so, that the preparation should contain $5 \times 10^8$-$10^{10}$, optimally $5 \times 10^9$ micro-organism cells, then the wet preparation or the preparation dried at a temperature below 40° C., in quantity 2 and 20, optimally in the quantity of 5 kg/ha was applied in the soil to be treated. Optimally at least $10^{13}$ micro-organism cells pro hectare were incorporated in the soil.

SUMMARY

Subject of the invention is products and procedure for the treatment of the soil with bacteria for the improvement of the growth of the plants and for increasing the yields, procedures for making the products, micro-organism stocks serving as a basis of the products, multiplying at low temperature, biosynthetizing polysaccharides, and procedure for the production of these. One of the micro-organism cells according to the invention or a compound of these, will be transported to the soil or fixed the seeds of the plants.

With the procedure according to the invention a product will be transported to the soil, which product contains at least one of the soil-bacterium groups transforming the nitrogen of the air into compounds available for the plants, solubilising the mineralised phosphate- and potassium compounds and biosynthetising the materials improving the vegetal development, producing polysaccharides optimally influencing the structure of the soil, isolated from various soils and altered in laboratory, so satisfactory yields will be reached, practically excluding the application of the expensive fertilizers.

The invention claimed is:

1. A preparation suitable for treatment of soil and plant seeds, which comprises a biologically pure culture of at least one living microorganism capable of propagating in different soil types in the environment of a plant, wherein one of said at least one microorganism is *Bacillus megaterium* var. M326 (deposited under NCAIM accession number NCAIM /P/ B001291) and said preparation comprises $5 \times 10^6$ to $5 \times 10^{11}$ cells/gram of said preparation.

2. The preparation according to claim 1, wherein said preparation comprises agriculturally acceptable wet or dry carriers non-toxic for said at least one microorganism.

3. The preparation according to claim 1, wherein said preparation comprises at least one of the following substances selected from the group consisting of water, soy flour, starch, and glucose, as carrier.

4. The preparation according to claim 1, wherein said preparation also comprises at least one microorganism selected from the strains *Azospirillum brasilense* ssp. SW51 (deposited under NCAIM accession number NCAIM /P/ B 001293), *Azotobacter vinelandii* ssp. M657 (deposited under NCAIM accession number NCAIM /P/B 001292), *Pseudomonas fluorescens* var. SW11 (deposited under NCAIM accession number NCAIM /P/ B 001296), *Bacillus polymyxa* var. SW17 (deposited under NCAIM accession number NCAIM /P/ B 001295), *Micrococcus roseus* ssp. A21 (deposited under NCAIM accession number NCAIM /P/B 001294), *Bradyrhizobium japonicum* var. PH25 (deposited under NCAIM accession number NCAIM /P/ B 001302), or

*Streptomyces albus* var. 0003 LP (deposited under NCAIM accession number NCAIM /P/ B 001301).

5. The preparation according to claim 1, wherein said preparation comprises $10^7$ to $10^{10}$ cells/gram of said preparation.

6. The preparation according to claim 1, wherein said at least one microorganism can propagate at temperature below 20° C.

7. The preparation according to claim 1, wherein said at least one microorganism can propagate in soils with a pH below 5.0.

8. A process for preparing a preparation suitable for the treatment of soil and plant seeds, characterized by cultivating separately or together, in a culture medium containing a carbon source and a nitrogen source and inorganic salts, a biologically pure culture of at least one microorganism that can propagate at low temperature and in soils with low pH until reaching between $5\times10^7$ and $5\times10^9$ cells per milliliter, wherein one of said at least one microorganism is *Bacillus megaterium* var. M326 (deposited under NCAIM accession number NCAIM /P/ B001291).

9. The process according to claim 8, further comprising freeze drying the culture or cultures obtained.

10. The process according to claim 8, wherein said carbon source is glucose; and said nitrogen source is selected from the group consisting of ammonium nitrate, ammonium sulphate, corn steep liquor, and casein-hydrolyzate; and said inorganic salt is calcium carbonate.

11. A biologically pure culture of the microorganism *Bacillus megaterium* var. M326, deposited in the National Collection of the Agricultural and Industrial Microorganisms (NCAIM) under the depository accession number NCAIM / P/ B 001291.

12. A process for soil treatment comprising applying a preparation comprising a biologically pure culture of at least one microorganism wherein one of said at least one microorganism is *Bacillus megaterium* var. M326 (deposited under NCAIM accession number NCAIM /P/ B001291), in quantities of between $10^{10}$ and $10^{14}$ cells per hectare on or in the soil, in frost-free period.

13. The process according to claim 12, wherein said quantity is between $10^{11}$ and $10^{12}$ cells per hectare.

14. The process according to claim 12, wherein said preparation comprises at least one of the following substances selected from the group consisting of water, soy flour, starch, and glucose, as carrier.

15. A process for the treatment of plant seeds comprising treating the seeds with a liquid product comprising a biologically pure culture of at least one microorganism, wherein one of said at least one microorganism is *Bacillus megaterium* var. M326 (deposited under NCAIM accession number NCAIM /P/ B001291) and said liquid product comprises $5\times10^6$ to $5\times10^{11}$ cells/gram of said liquid product.

16. The process according to claim 15, wherein said preparation comprises at least one of the following substances selected from the group consisting of water, soy flour, starch, and glucose, as carrier.

* * * * *

UNITED STATES PATENT AND TRADEMARK OFFICE
CERTIFICATE OF CORRECTION

PATENT NO. : 7,842,494 B2
APPLICATION NO. : 10/486747
DATED : November 30, 2010
INVENTOR(S) : Gyorgy Botond Kiss et al.

It is certified that error appears in the above-identified patent and that said Letters Patent is hereby corrected as shown below:

<u>Column 1, and Title Page item 54</u>
Line 1, "MICRO-ORGANISMS" should read --MICROORGANISMS--.

<u>Column 9,</u>
Lines 53-57, "sterile 1N NaOH solution.

L-malic acid  5.0 g"

should read

--sterile 1N NaOH solution.

The composition of the Nfb(II) medium is as follows:

L-malic acid  5.0 g--

<u>Column 10,</u>
Lines 59-62, "this culture.

Bacto trypton (Difco)  1.0%"

should read

--this culture.

Composition of the Tag medium is as follows:

Bacto trypton (Difco)  1.0%--.

Signed and Sealed this
First Day of March, 2011

David J. Kappos
*Director of the United States Patent and Trademark Office*

Column 14,
Line 7, "Microorganisms" should read --microorganisms--.